United States Patent
Maeda

(10) Patent No.: US 8,603,826 B2
(45) Date of Patent: Dec. 10, 2013

(54) METHOD OF FORMING TISSUE STRUCTURE IMAGE OF PROCESSED FOOD OR RAW MATERIAL FOR PRODUCING THE SAME

(75) Inventor: Tatsurou Maeda, Fujimino (JP)

(73) Assignee: Nisshin Seifun Group Inc., Tokyo (JP)

( * ) Notice: Subject to any disclaimer, the term of this patent is extended or adjusted under 35 U.S.C. 154(b) by 760 days.

(21) Appl. No.: 12/448,609

(22) PCT Filed: Dec. 25, 2007

(86) PCT No.: PCT/JP2007/074877
§ 371 (c)(1),
(2), (4) Date: Oct. 19, 2009

(87) PCT Pub. No.: WO2008/078752
PCT Pub. Date: Jul. 3, 2008

(65) Prior Publication Data
US 2010/0035348 A1    Feb. 11, 2010

(30) Foreign Application Priority Data

Dec. 27, 2006  (JP) .................................. 2006-353478
Dec. 21, 2007  (JP) .................................. 2007-329624

(51) Int. Cl.
*G01N 33/02*   (2006.01)
*C07C 211/00*  (2006.01)

(52) U.S. Cl.
USPC ............................. 436/20; 568/716; 564/305

(58) Field of Classification Search
USPC ............................. 436/20; 564/305; 568/716
See application file for complete search history.

(56) References Cited

U.S. PATENT DOCUMENTS 5,424,000 A * 6/1995 Winicov et al. ............... 510/100
5,658,798 A   8/1997 Bertin et al.
6,720,185 B2 * 4/2004 Maeda et al. .................... 436/20

FOREIGN PATENT DOCUMENTS

| JP | 9-243561 A | 9/1997 |
| JP | 10-123054  | 5/1998 |
| JP | 2001-208745 | 8/2001 |

(Continued)

OTHER PUBLICATIONS

M. B. Dürrenberger, et al., Visuaization of Food Structure by Confocal Laser Scanning Microscopy (CLSM), Lebensmittel-Wissenschaft und-Technologie, 2001, vol. 34, Issue 1, pp. 11-17.

(Continued)

*Primary Examiner* — Krishnan S Menon
*Assistant Examiner* — Rebecca M Fritchman
(74) *Attorney, Agent, or Firm* — Kubovcik & Kubovcik

(57) ABSTRACT

A method is provided that can form a clear textural structure image of a processed food or a raw material for the processed. Also, said method can form an image clear enough to clearly discern even an intertwined structure of starches, proteins and lipids of a processed food or a raw material for the processed food. The method includes light-exciting the processed food or the raw material for the processed food which is stained with a fluorescent dye having triphenylmethane skeleton; collecting data about the light-excited processed food or the light-excited raw material using at least three kinds of monitoring lights, that is, a monitoring light A having a fluorescence wavelength of 380 nm or longer and shorter than 450 nm, a monitoring light B having a fluorescence wavelength of 450 nm or longer and shorter than 560 nm, and a monitoring light C having a fluorescence wavelength of 560 nm to 700 nm; and forming an image on the basis of the collected data.

4 Claims, 6 Drawing Sheets

(56) References Cited

FOREIGN PATENT DOCUMENTS

| | | |
|---|---|---|
| JP | 2002-323449 A | 11/2002 |
| JP | 2003-294626 A | 10/2003 |

OTHER PUBLICATIONS

Tadahiko Hoshino, et al., Chapter 5, Part. 3. Wheat Flour, Food Histology, Koseikan Co., Ltd., pp. 213-218, 1998.

* cited by examiner

METHOD OF FORMING TISSUE STRUCTURE IMAGE OF PROCESSED FOOD OR RAW MATERIAL FOR PRODUCING THE SAME

BACKGROUND OF THE INVENTION

1. Field of the Invention

The present invention relates to a method for forming a textural structure image of a processed food or a raw material for the processed food. The present invention also relates to a fluorescent dye used for forming a textural structure image of a processed food or a raw material for the processed food.

2. Description of the Related Art

From the earliest times, a variety of foods have been known, and vast amounts of researches are still underway to meet the demand for tasty foods. This is also true for processed foods—particularly for processed foods derived from a grain, and more particularly for secondary processed foods, such as breads, noodles, cooked rice, confectioneries, and a surface layer of tempuras, whose principal raw material is wheat flour or rice, which opens avenues of study and research for providing savory processed foods to be conducted.

For example, since taste perception and oral perception have a great effect on the taste of foods, taste perception and oral perception of foods have been researched. As a result, particularly for secondary processed foods, it has been considered that taste perception and oral perception of foods are greatly affected by what form of starches, proteins, and lipids (that are accepted to be three major nutrients) exist in the foods.

Conventionally, taste perception and oral perception of foods have been evaluated only through sensory testing by professional panels. In recent years, attempts have been made to form an image (textural structure image) showing the textural structure (tissue structure) of a food using various apparatuses and devices, and to determine taste perception from the thus-displayed textural structure. However, observation of textural structure obtained from using such apparatuses and devices does not always yield satisfactory evaluation results because borders between respective components of food are unclear, and obtained images are planar.

For example, in the case of observation using an electron microscope, the textural structure of a specimen is observed by applying an electron beam to the specimen and then detecting the reflected electrons (scanning electron microscopy). This method enables observation of the specimen at very high resolution. However, since this method does not permit staining of the sample, discriminating specific components is difficult, and thus structural analysis of borders between the components is also difficult. In the case of observation through an optical microscope, the textural structure of a specimen is observed after staining specific components of a slice to obtain the specimen. However, this method also provides unclear borders between the respective components. Multi-staining may be performed to improve the clearness of the borders between the specific components. Such a multi-staining improves color segmentation of the specific components. However, discernment of the textural structure remains virtually impossible because staining specificity of the specific components is low, and dyes overlap the specific components (Non-Patent Document 1).

The method for observing a textural structure of a specimen after staining specific components of a specimen by joint use of fluorescence observation and non-fluorescence observation including phase contrast observation, differential interference observation, and the like provides a very clear image in comparison to the conventional method. However, the method is still unsatisfactory in that, for example, it fails to provide clear discernment of intertwined starches, proteins and lipids (Patent Documents 1 and 2).

Patent Document 1: Japanese Patent Application Laid-Open (JP-A) No. 2002-323449

Patent Document 2: Japanese Patent Application Laid-Open (JP-A) No. 2003-294626

Non-Patent Document 1: *Food Histology* (p. 213~). Koseikan Co., Ltd., Tadahiko Hoshino and two others, published Jun. 5, 1998

SUMMARY OF THE INVENTION

The present invention is directed to a method for forming a clear textural structure image of a processed food or a raw material for the processed food, and particularly, a clear textural structure image of a secondary processed food or a raw material for the secondary processed food. The present invention is also directed to a method for forming an image clear enough to clearly discern even an intertwined structure (hereinafter, sometimes referred to as "microstructure") of starches, proteins and lipids of a processed food or a raw material for the processed food.

The present inventor has performed extensive studies regarding the above-mentioned subjects. As a result, the inventor surprisingly found that an extremely clear image can be obtained by preparing a slice from a raw material for a secondary processed food through a typical method, staining the slice with a fluorescent dye, radiating an excitation light thereto, and then observing the stained specimen (hereinafter sometimes referred to as "specimen") by use of a monitoring light consisting of a plurality of monitoring lights having respective specific fluorescence wavelengths, or through forming an image on the basis of the obtained data through a typical method. The inventor also found that image clearness can be improved further by using a specific fluorescent dye. In addition, the inventor found that the clearness of the image can be further enhanced by regulating the nonfreezing water content of the specimen to below a certain value before performing slicing. The inventor's extensive studies based on these findings resulted in completion of the present invention.

The invention of Claim 1 provides a method for forming a textural structure image of a processed food or a raw material for the processed food. The method includes light-exciting the processed food or the raw material for the processed food which is stained with a fluorescent dye having triphenylmethane skeleton; collecting data about the light-excited processed food or the light-excited raw material using at least three kinds of monitoring lights, that is, a monitoring light A having a fluorescence wavelength of 380 nm or longer and shorter than 450 nm, a monitoring light B having a fluorescence wavelength of 450 nm or longer and shorter than 560 nm, and a monitoring light C having a fluorescence wavelength of 560 nm to 700 nm; and forming an image on the basis of the collected data. The invention also provides a method for forming a textural structure image of a processed food or a raw material for the processed food, wherein the image is formed by observing all the data obtained by the three or more kinds of monitoring lights substantially at the same time, or the image is formed on the basis of the independently obtained data. The monitoring light means a light that is used for collecting data constituting the image that shows the textural structure of a processed food or a raw material for the processed food. In the present invention, monitoring lights having a fluorescence wavelength other than the above-described fluorescence wavelengths may also be used in combination with any of the three kinds of monitoring lights. Such an additional monitoring light may be selected from among fluorescent lights having a variety of fluorescence wavelengths. The lights having fluorescence wavelengths additionally used are not limited to a certain value. An examples of the lights having additionally used is lights having fluorescence wavelengths of longer than 700 nm or shorter than 380 nm.

The invention of Claim 2 provides the method according to Claim 1, wherein slicing is performed with controlling the nonfreezing water content in the slice to 30% by weight or less before radiating an excitation light to the specimen obtained from the slice of the processed food or the raw material of the processed food. More specifically, the processed food or the raw material for the processed food for forming a textural structure image is frozen and fixed to control its nonfreezing water content to 30% by weight or less. Then, it is sliced by use of a microtome or a cryostat, and stained with a fluorescent dye. The nonfreezing water as used herein means water remaining unfrozen in the processed food or the raw material for the processed food even when the processed food or the raw material for the processed food is frozen.

The invention of Claim 3 provides the method according to Claim 1 or 2, wherein the processed food is a secondary processed food derived from a grain, and the raw material for the processed food is a grain or a primary processed food to be subsequently subjected to a secondary food processing.

The invention of Claim 4 provides a fluorescent dye for forming an image that shows a textural structure of a processed food or a raw material for the processed food, the fluorescent dye being expressed by Formula 1:

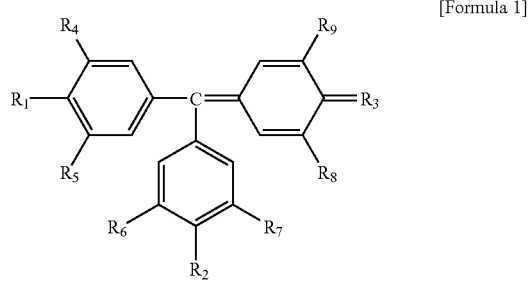

[Formula 1]

(wherein, $R_1$ and $R_2$ each represents $NH_2$, NHY, $NY^1Y^2$, or OH, $R_3$ represents O, $NH_2$, NHY, or $NY^1Y^2$, $R_4$, $R_5$, $R_6$, $R_7$, $R_8$, and $R_9$ each represents one selected from H, $C_nH_{2n+1}$, $SO_3X$, and COOX, X represents H or an alkali metal atom, Y, $Y^1$, and $Y^2$ each represents an alkyl group having a carbon number of 1 to 3, or a phenyl group which may have a substituent, and n represents an integer of 1 to 3). The fluorescent dye may be used alone or as a mixture. The invention also provides a fluorescent dye according to Claim 4, for visualizing a textural structure of a starch and a protein of a processed food or a raw material for the processed food, or for visualizing a textural structure of a starch, a protein, and a lipid of a processed food or a raw material for the processed food.

Hereinafter, the present invention will be described in detail.

The processed food in the present invention is not particularly limited as long as it is manufactured by processing food raw materials using any means and methods. Examples of the processed food include a primary processed food and a secondary processed food, and the secondary processed food is more preferable. A specific example of the primary processed food is a primary processed food of grains including wheat flour, durum wheat flour, sorghum flour, barley flour, polished barley or wheat, oat flour, rye flour, corn flour, barnyard millet flour, millet flour, Indian millet flour, starch derived from a grain, protein derived from a grain, and the like. A specific example of the secondary processed food manufactured by applying various means and methods to the primary processed food is a secondary processed food of a grain including breads, noodles, confectionery, hus (dried bread-like pieces of wheat gluten), pastas, fries, broils, steamed foods, and the like. An example of the noodles is udon (a kind of Japanese wheat noodle), hiyamugi (a kind of Japanese wheat noodle), somen (vermicelli-like Japanese wheat noodle), and the like.

An example of the raw material for the processed food in the present invention is a food raw material. A particularly preferable example of the raw material is a grain. Examples of the raw material include a primary processed food to be subsequently subjected to a secondary food processing. Preferable examples of the raw material include, for example, dough for breads, noodle strand for boiling noodles, wet gluten for hus manufactured by kneading a dough, dough for foods, such as a biscuit, and the like. The secondary processed food may be manufactured by well known manufacturing processes.

Many researches have been conducted on the textural structure of the processed food or the raw material for the processed food of the invention, providing a lot of reports thereon. The textural structure image of the invention indicates an image showing the textural structure of a processed food or a raw material for the processed food, including the reported textural structures. The invention particularly relates to a textural structure image of a secondary processed food derived from a grain, a grain as a raw material for the secondary processed food, or a primary processed food to be subsequently subjected to a secondary food processing. The textural structure image, also, means a tissure structure image or an internal tissue structure image. For a bread dough which is one of the raw material for the secondary processed food, specific examples of the textural structure include the existing form of starch granules and gluten proteins which constitute the bread dough, and the existing form of starch granules, gluten proteins, and lipids. In addition, the intertwining form of gluten proteins and starch granules greatly affecting taste perception and oral perception may also be a specific example of the textural structure. For reference, the textural structure of the processed food and the raw material for the processed food is not limited to the above-mentioned specific examples.

According to the present invention, a slice is prepared from the processed food or the raw material for the processed food, and then the slice sample is stained with a fluorescent dye, whereby a stained sample is prepared. In the preparation of the slice, although there are several known fixation methods, the fixation method is not particularly limited thereto. Here, in order to fix a processed food or a raw material for the processed food, it is important to perform slicing by use of a microtome or a cryostat after controlling the nonfreezing water content to 30% by weight or less.

In addition, among the fixation methods for obtaining a slice, freeze-conserving the processed food or the raw material for the processed food is preferred. This is because, since the frozen-conserved processed food or raw material for the processed food is properly solid and properly viscoelastic, a slice or a sample obtained therefrom has a flat and smooth surface and thus makes it easy to obtain an image showing an internal texture therefrom.

It is preferable to freeze a processed food or a raw material for the processed food rapidly. The freezing temperature is not particularly limited, however, it is preferably set to −18° C. or less, and more preferably to −22° C. or less.

A method for preparing the slice is not particularly limited. For example, freezing fixation, immersion fixation, or microwave fixation may be employed. As an example, the freezing fixation method will be described below. A specimen prepared from the processed food or the raw material for the processed food is freeze-fixed on a cooling stage of a microtome. The freeze-fixed specimen is sliced to a predetermined thickness. Each of the slices is placed on a prepared slide and dry-fixed by use of a heater, for fixation.

In the case of microwave fixation, a food is immersed in, for example, a glutaraldehyde solution for 12 to 24 hours, and then is irradiated with microwave for 10 to 60 seconds for fixation.

One of the characteristics of the present invention is to stain the slice with a fluorescent dye having a triphenylmethane skeleton. In the fluorescent dye having the triphenylmethane skeleton, the triphenylmethane skeleton may be expressed by the following general formula:

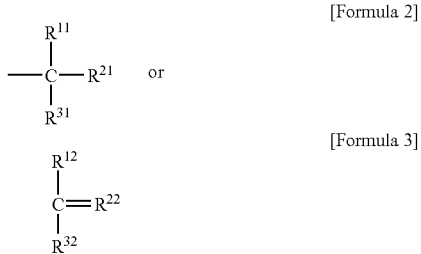

[Formula 2]

[Formula 3]

(wherein, $R^{11}$, $R^{21}$, $R^{31}$, $R^{12}$, $R^{22}$, $R^{32}$ each represents a phenyl group which may be substituted by a group selected from $NH_2$, NHY, $NY^1Y^2$, OH, O, $C_nH_{2n+1}$, $SO_3X$, and COOX, X represents H or an alkali metal atom, Y, $Y^1$, and $Y^2$ each represents an alkyl group having a carbon number of 1 to 3, or a phenyl group which may have a substituent, and n represents an integer of 1 to 3. Here, examples of the substituent include $SO_3X$, COOX, a halogen atom, and the like). However, the fluorescent dye is not limited thereto, and, irrespective of the expression, any fluorescent dye can be used in the present invention as long as it has the triphenylmethane skeleton.

Preferable fluorescent dyes having a triphenylmethane skeleton include a fluorescent dye that is expressed by the following general formula:

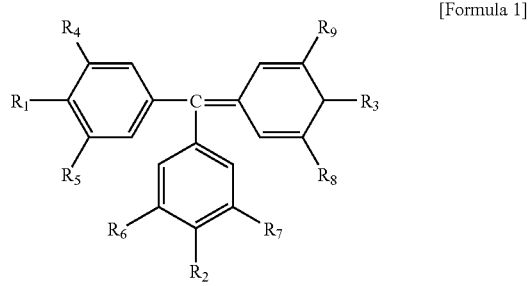

[Formula 1]

(wherein, $R_1$ and $R_2$ each represents $NH_2$, NHY, $NY^1Y^2$, or OH, $R_3$ represents O, $NH_2$, NHY, or $NY^1Y^2$, $R_4$, $R_5$, $R_6$, $R_7$, $R_8$, and $R_9$ each represents one selected from H, $C_nH_{2n+1}$, $SO_3X$, and COOX, X represents H or an alkali metal atom, Y, $Y^1$, and $Y^2$ each represents an alkyl group having a carbon number of 1 to 3, or a phenyl group which may have a substituent, and n represents an integer of 1 to 3. Here, examples of the substituent include $SO_3X$, COOX, a halogen atom, and the like).

In the above formula, the alkali metal atom of X is preferably a sodium atom or a potassium atom, and n is preferably 1. In addition, when $R_3$ is $NH_2$, one of $R_4$, $R_5$, $R_6$, $R_7$, $R_8$, and $R_9$ is $SO_3^-$ or $COO^-$, and the dye may be expressed as being electrically neutral. Furthermore, the dye is one that is known as a fluorescent dye with a triphenylmethane skeleton. There is a plurality of methods for expressing the chemical structure of the dye, and the dye may be expressed by another formula according to the expression methods. The present invention includes any fluorescent dye having a triphenylmethane skeleton and expressed by such expression methods.

Among the above-described compounds, particularly among the compounds expressed by Formula 1, a compound (hereinafter, referred to as "compound A") where $R_1$, $R_2$ and $R_3$ each is $NH_2$, and $R_4$, $R_5$, $R_6$, $R_7$, $R_8$, and $R_9$ each is as described above, or a compound (hereinafter, referred to as "compound B") where $R_1$ and $R_2$ each is OH, $R_3$ is O, and $R_4$, $R_5$, $R_6$, $R_7$, $R_8$, and $R_9$ each is as described above is preferable.

Among the compounds A, a compound (hereinafter, referred to as "compound AA") where $R_1$, $R_2$ and $R_3$ each is $NH_2$, and $R_4$, $R_5$, $R_6$, $R_7$, $R_8$ and $R_9$ each is one selected from H, $CH_3$ and $SO_3Na$, or a compound (hereinafter, referred to as "compound BB") where $R_1$ and $R_2$ each is OH, $R_3$ is O, and $R_4$, $R_5$, $R_6$, $R_7$, $R_8$ and $R_9$ each is one selected from H, $CH_3$ and COONa is preferable.

Specific examples of the compound AA include a compound (Rosaniline) where $R_1$, $R_2$ and $R_3$ each is $NH_2$, $R_6$ is $CH_3$, and $R_4$, $R_5$, $R_7$, $R_8$ and $R_9$ each is H, a compound (Magenta II) where $R_1$, $R_2$ and $R_3$ each is $NH_2$, and $R_5$ and $R_6$ each is $CH_3$, and $R_4$, $R_7$, $R_8$ and $R_9$ each is H, a compound (New fuchsin) where $R_1$, $R_2$ and $R_3$ each is $NH_2$, $R_5$, $R_6$ and $R_8$ each is $CH_3$, and $R_4$, $R_7$ and $R_9$ each is H, a compound (Acid fuchsin) where $R_1$, $R_2$ and $R_3$ each is $NH_2$, $R_4$, $R_6$ and $R_9$ each is $SO_3Na$, $R_5$ is $CH_3$, and $R_7$ and $R_8$ each is H, and a compound (Pararosaniline) where $R_1$, $R_2$ and $R_3$ each is $NH_2$, and $R_4$, $R_5$, $R_6$, $R_7$, $R_8$ and $R_9$ each is H. Specific examples of the compound BB include a compound (Aluminon) where $R_1$ and $R_2$ each is OH, $R_3$ is O, $R_4$, $R_6$ and $R_8$ each is COONa, and $R_5$, $R_7$ and $R_9$ each is H. However, the compound AA and the compounds BB are not limited thereto.

In the present invention, staining may be performed through use of one fluorescent dye, or alternatively through use of two or more fluorescent dyes. In addition, the fluorescent dye(s) may be used in combination with other fluorescent dye(s) or non-fluorescent dye(s) as long as it (they) can form a clear image.

A method for preparing the staining solution is not particularly limited as long as the method makes use of the fluorescent dye. For example, the fluorescent dye solution of a commonly-used density is regulated by use of well-known solvent, and then staining is performed on a specimen by use of the regulated fluorescent dye solution. Here, the staining conditions are not particularly limited. For a specific example, the slice is allowed to react with the fluorescent dye solution for a predetermined duration (for example, for 1 minute to 30 minutes; or, when reaction for a longer time is desired, for 1 hour to 3 hours), followed by drying. The dried specimen slice is embedded in a soft Canadian balsam, whereby a specimen is prepared. The above-described method is merely illustrative, and it should not be taken in a limiting sense.

The stained specimen obtained as described above will be subsequently subjected to irradiation with an excitation light. In the present invention, it is preferable that the processed food, the raw material for the processed food, or the sample is conserved at a freezing temperature, and the nonfreezing water content in the sample is 30% by weight or less. In addition, it is preferable that the freezing temperature is set to −18° C. or less, and the nonfreezing water content is 25% by weight or less, and it is more preferable that the freezing temperature is set to −22° C. or less, and the nonfreezing water content is 20% by weight or less. By setting the nonfreezing water content as described above, the clearness of the texture image to be obtained can be improved, which is very advantageous.

For reference, the nonfreezing water as used herein means the water that can freely migrate in the processed food or the raw material for the processed food when the processed food or the raw material for the processed food is conserved at a temperature of 0° C. or less. In the present invention, the nonfreezing water is the water having a mobility where a relaxation time, T2, is greater than 30 μs, and the freezing water is the water having a mobility smaller than 30 μs. The content of the nonfreezing water can be measured by a variety of methods. In the present invention, the nonfreezing water content is measured by a nuclear magnetic resonance method, and more particularly, by a pulsed NMR method. In more specific, the nonfreezing water content may be determined by measuring $^1$H (proton) relaxation time, T2, and $^1$H (proton) abundance ratio through a solid echo method (90°-T-90°-T pulse) by use of JNM-MU25 (JEOL Ltd.).

In the irradiation with an excitation light, a mercury lamp (100 V), a mercury lamp (200 V), a xenon lamp (75 V), a xenon lamp (150 V), a halogen lamp (12 V 100 W), or a tungsten lamp (6 V 30 W) may be employed as an excitation light source. Other than these lamps, a xenon lamp (wavelength 250 nm to 1,000 nm), a tungsten lamp (wavelength 250 nm to 1,000 nm), a Cr:LiSAF lamp (wavelength 430 nm), a helium-cadmium laser (wavelength 325 nm, 442 nm), a UV argon laser (wavelength 351 nm, 364 nm), an argon ion laser (wavelength 488 nm, 514 nm), Nd:YAG laser (wavelength 532 nm), a helium neon laser (wavelength 543 nm, 594 nm, 633 nm), a krypton ion laser (wavelength 568 nm, 647 nm), and the like may also be employed as an excitation light source. Among them, particularly preferable is the UV argon laser (wavelength 351 nm, 364 nm) and the like that has an excitation wavelength of 420 nm or shorter.

In the treatment of the excitation, it is preferable that the excitation light passes through a filter to align the wavelength of the excitation light. An excitation filter (330 nm to 385 nm) may be employed as the filter.

The irradiation conditions including irradiation time and irradiation level cannot be specified by rule because they are selected according to the kind of the fluorescent dye, the densities of the solvent and the fluorescent dye in the solution, and the like. For example, the irradiation time and the irradiation level may be 30 seconds, and 0.3 mW/cm$^2$, respectively.

After the irradiation with an excitation light, the specimen is observed under a fluorescence microscope by use of a plurality of monitoring lights. That is, a plurality of monitoring lights with certain fluorescence wavelengths is combined together. The specimen subjected to the irradiation with an excitation light is observed under a fluorescence microscope by use of the combined monitoring light. Then, an image can be obtained by a typical method on the basis of the observation result. Although the monitoring light, which is one of the principal characteristics of the present invention, has been briefly described above, it will be described in more detail herebelow.

The monitoring light having a fluorescence wavelength of 380 nm or longer and shorter than 450 nm may have either a very narrow range of wavelength or a wide range of wavelength as long as the fluorescence wavelength thereof is 380 nm or longer and shorter than 450 nm. For example, a monitoring light having a fluorescence wavelength of 400 nm, 405 nm, 420 nm, or 440 nm, and a monitoring light having a fluorescence wavelength of 380 nm to 385 nm may be employed as the monitoring light. In addition, the monitoring light includes a monitoring light whose fluorescence wavelength includes a part of the wavelength range of 380 nm or longer and shorter than 450 nm. For example, a monitoring light having a fluorescence wavelength of 350 nm or longer and 385 nm or shorter may be employed as the monitoring light.

Each of the cases of the monitoring light having a fluorescence wavelength of 450 nm or longer and shorter than 560 nm and the monitoring light having a fluorescence wavelength of 560 nm to 700 nm is the same as the above-described case of the monitoring light having a fluorescence wavelength of 380 nm or longer and shorter than 450 nm.

In the present invention, not only the above mentioned three kinds of monitoring lights, but also monitoring lights having different fluorescence wavelengths may be used in combination. The fluorescence wavelength of the monitoring lights used in combination may fall either within the range of 380 nm to 700 nm, or out of the range of 380 nm to 700 nm. For example, a monitoring light having a fluorescence wavelength of 405 nm may be used in combination with a monitoring light having a fluorescence wavelength of 420 nm. Two or more kinds of monitoring lights having fluorescence wavelengths within the range of 380 nm to 450 nm may also be used in combination. This is also true for the monitoring lights having fluorescence wavelengths of 450 nm or longer and shorter than 560 nm and 560 nm to 700 nm, respectively.

The above-mentioned monitoring light may be regulated by well-known means and methods. That is, it may be regulated, for example, by filtering the emitted fluorescent light.

An image of the textural structure of the processed food or the raw material (hereinafter, sometimes referred to as "processed food") for the processed food can be formed by use of typical methods, on the basis of the data obtained by the above-mentioned monitoring light. Means for obtaining the image is not limited. In more specific, by accumulating data from the observation results of respective monitoring lights, it is possible to obtain the image by use of a typical method. In addition, the image can be obtained through image formation by use of a microscope, and the image can also be obtained by use of well-known technologies including photographic methods. Furthermore, by performing image treatments on the obtained images, it is also possible to form an image providing stereoscopic visualization. The visualization method is not particularly limited, and any means and methods can be employed as long as they can provide a view showing an internal textural structure of the food.

In the present invention, a structure of an internal texture can be observed by transforming the observed data into electric signals through use of a specific observation apparatus and processing the transformed electric signals with a computer. It is also true when the observation is performed within an infrared or ultraviolet wavelength range.

Through the analysis of the obtained image, the textural structure of the processed food can be found. Such an analysis method is not particularly limited, and any method, such as a method for observing the structure with the naked eye, and a method for analyzing data obtained through various treatments on the basis of the image data, can be employed as long as it provides an understanding of the structure of the internal texture of the processed food. For example, it is possible to display a stereoscopic view of the microstructure of the internal texture, for visualization. In addition, it is also possible to form a digital image and analyze the digital image to thereby digitize and quantify the result.

According to the present invention, it is possible to form a clear image which shows an internal textural structure or an internal textural microstructure of a processed food. The clearness of the image is such an extent that borders between starches, proteins and lipids constituting the processed food are clear and the microstructure of the internal texture can be discriminated.

Examples of the processed food whose clear image can be obtained according to the present invention include a secondary processed food of a grain, and examples of the raw material for the processed food include a grain and a primary processed food of a grain, which will be subsequently subjected to the secondary food processing. Particularly suitable for the present invention are breads, noodles, such as udon (a kind of Japanese wheat noodle), hiyamugi (a kind of Japanese wheat noodle), and somen (vermicelli-like Japanese wheat noodle), hus (dried bread-like pieces of wheat gluten), confectionery, and the like. In addition, preferable examples thereof include wheat flours, secondary processed foods that are obtained by applying various means and methods thereto, and primary processed foods to be subsequently subjected to a secondary food processing. Particularly, it is possible to discriminate a network structure of glutens of a bread dough and correlation between glutens and starch particles.

Considering that the conventional fluorescence observation is incapable of discriminating the internal textural structure, the present invention is eminently practical.

DETAILED DESCRIPTION OF THE EXEMPLARY EMBODIMENTS

Figure 1:
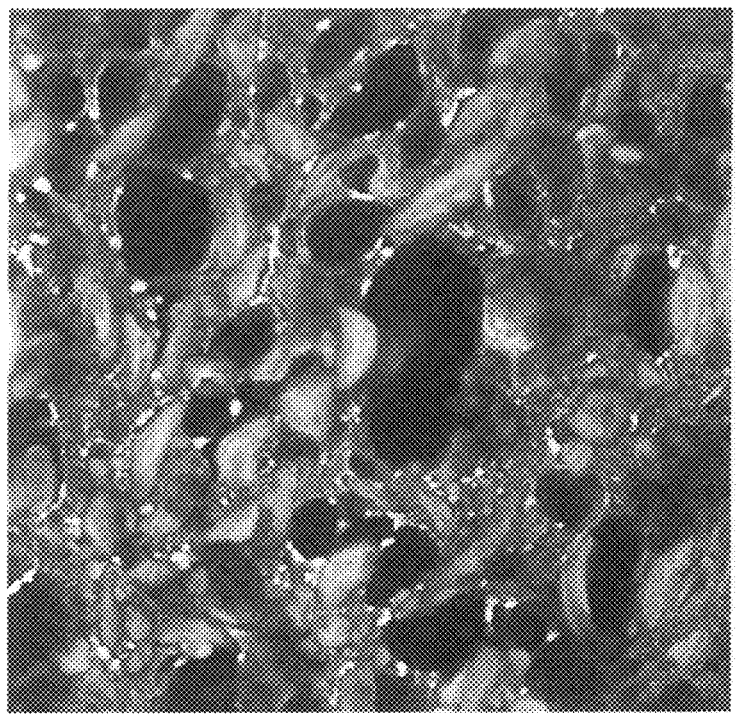
FIG. 1 is an image illustrating a texture of a boiled spaghetti, which is obtained according to a method of Example 1 of the present invention.

Hereinafter, the present invention will be described in more detail with reference to examples, reference examples, and comparative examples, which should not be construed as limiting the invention thereto.

Reference Example 1

Preparation of Fluorescent Dye 3 g of Fast Green was added to 1000 ml of distilled water, and the mixture was stirred, whereby a uniform fluorescent dye was prepared.

Reference Example 2

Preparation of Fluorescent Dye 5 g of Magenta II (Acid Magenta) was added to 1000 ml of distilled water, and the mixture was stirred, whereby a uniform fluorescent dye was prepared.

Reference Example 3

Preparation of Fluorescent Dye 3 g of Nile Blue was added to 1000 ml of distilled water, and the mixture was stirred, whereby a uniform fluorescent dye was prepared.

Example 1

Formation of Image of Boiled Spaghetti

Preparation of Slice 100 g of Ma-Ma Spaghetti (1.7 mm diameter, Nisshin Foods Inc.) was boiled in a boiling bath for 8 minutes, immersed in cold water for 30 seconds, and removed water sufficiently. Total water content in the spaghetti after the boiling was controlled to 75%. The boiled spaghetti was rapidly frozen for 30 minutes in a quick-freezer (Hoshizaki Electric Co., Ltd.) which is set to $-50°$ C. The frozen spaghetti was left at $-23°$ C. in a room of a microtome (CM-1100, Leica Corp.) for a duration to give the boiled spaghetti having the nonfreezing water content of 17%. Thereafter, the boiled spaghetti was sliced to a thickness of 20 μm on a cooling stage, and freeze-fixed on a prepared slide for a microscope, whereby a frozen slice was prepared.

Method for Measuring Nonfreezing Water Content $^1$H (proton) relaxation time, T2, and $^1$H (proton) abundance ratio were measured through a solid echo method (90°-T-90°-T pulse) by use of JNM-MU25 (JEOL Ltd.). The measurement was performed under the following condition: measurement temperature range was $-70°$ C. to 0° C.; pulse width was 2.4 μs; delay time was 8.0 μs; repetition time was 4.0 s; and number of times of integration was 8 times.

Preparation of Specimen

The fluorescent dye (Magenta II) prepared in Reference Example 2 was placed in a 200 ml glass bottle, and the frozen slice was immersed in the fluorescent dye. After the stained slice was taken out of the glass bottle, extra dye over the surface was wiped away, and then the slice was dried in a draft to give the specimen. Thereafter, the specimen was irradiated (irradiance level 0.3 mW/cm$^2$) with an excitation light of UV argon laser (351 nm, 364 nm).

Image Formation

Fluorescence emitted from the irradiated specimen was observed under a fluorescence microscope by use of monitoring lights having fluorescence wavelengths of 420 nm, 520 nm, and 580 nm, respectively. The observation was performed through use of a confocal laser scanning microscope (FV1000, Olympus Optical Co., Ltd.). The images observed at each fluorescence wavelength were accumulated as digital data, whereby an image was obtained.

The obtained image is shown in FIG. 1.

As shown in FIG. 1, borders between starches and proteins constituting the internal texture of the spaghetti are clear, and network structure of glutens and correlation between glutens and starch particles can be discriminated easily and clearly, making it possible to discern the structure of the internal texture. This shows us that the present invention can provide a clear image of the internal texture of the spaghetti.

Comparative Example 1

Formation of Image of Boiled Spaghetti

A specimen was prepared in a manner similar to that described in Example 1 by use of the frozen slice as described in Example 1 and the fluorescent dye as described in Reference Example 1. The specimen was irradiated with a UV argon laser in a manner similar to that described in Example 1. Thereafter, the fluorescence emitted from the irradiated specimen was observed under a fluorescence microscope in a manner similar to that described in Example 1. Here, monitoring lights of 520 nm, 560 nm and 580 nm were used. An image of the spaghetti was obtained in a manner similar to that described in Example 1.

Figure 2:
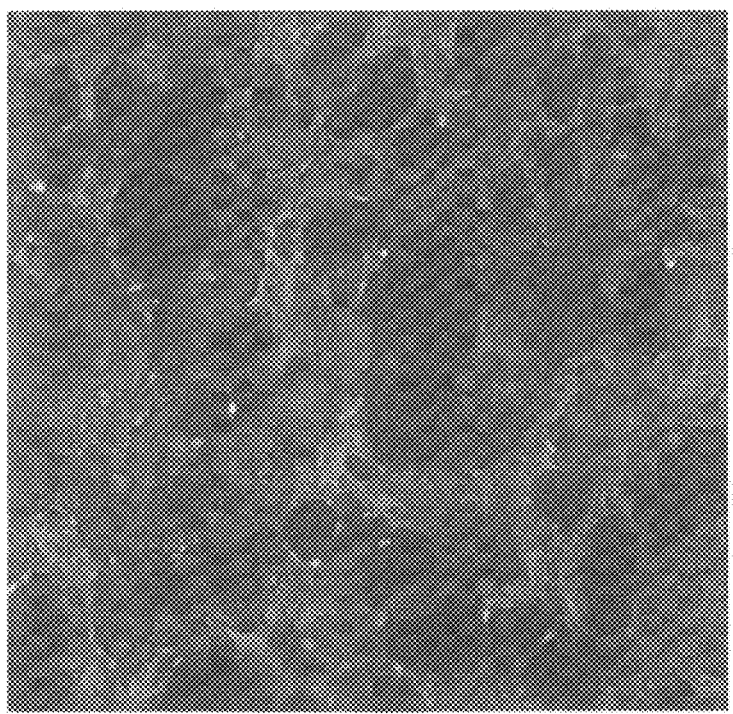
FIG. 2 is an image illustrating a texture of a boiled spaghetti, which is obtained according to a method of Comparative Example 1.

The obtained image is shown in FIG. 2.

As shown in FIG. 2, borders between starches and proteins constituting the internal texture of the spaghetti are unclear, and network structure of glutens and correlation between glutens and starch particles cannot be easily discriminated.

Comparative Example 2

Boiled Spaghetti

A specimen was prepared in a manner similar to that described in Example 1 by use of the frozen slice as described in Example 1 and the fluorescent dye as described in Reference Example 2. The specimen was irradiated with a UV argon laser in a manner similar to that described in Example 1. Thereafter, the fluorescence emitted from the irradiated specimen was observed under a fluorescence microscope in a manner similar to that described in Example 1. Here, monitoring lights of 420 nm, 580 nm and 620 nm were used. An image of the spaghetti was obtained in a manner similar to that described in Example 1.

Figure 3:
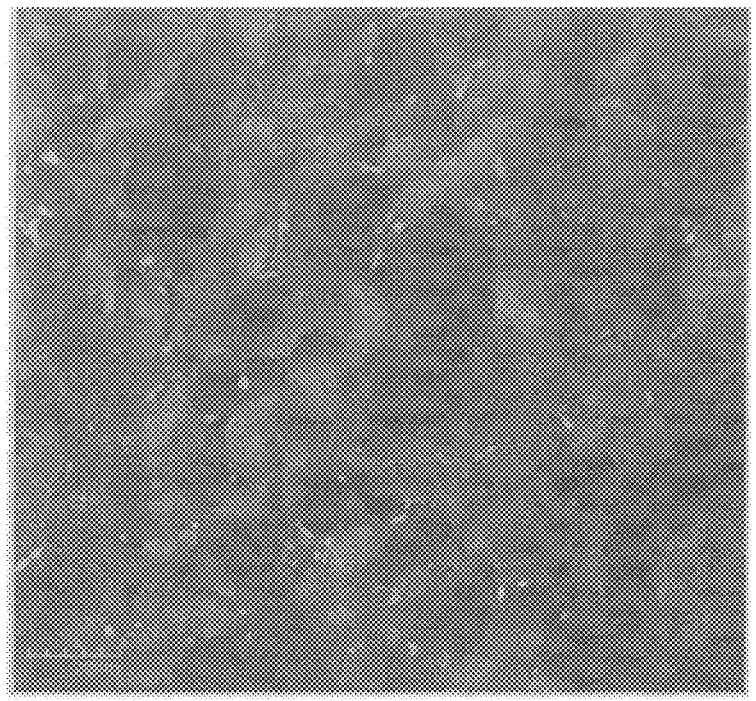
FIG. 3 is an image illustrating a texture of a boiled spaghetti, which is obtained according to a method of Comparative Example 2.

The obtained image is shown in FIG. 3.

As shown in FIG. 3, borders between starches and proteins constituting the internal texture of the spaghetti are unclear, and network structure of glutens and correlation between glutens and starch particles cannot be easily discriminated.

Comparative Example 3

Boiled Spaghetti

A specimen sample was prepared in a manner similar to that described in Example 1 by use of the frozen slice as described in Example 1 and the fluorescent dye as described in Reference Example 2. The specimen was irradiated with a UV argon laser in a manner similar to that described in Example 1. Thereafter, the fluorescence emitted from the irradiated specimen was observed under a fluorescence microscope in a manner similar to that described in Example 1. Here, monitoring lights of 420 nm, 520 nm and 560 nm were used. An image of the spaghetti was obtained in a manner similar to that described in Example 1.

Figure 4:
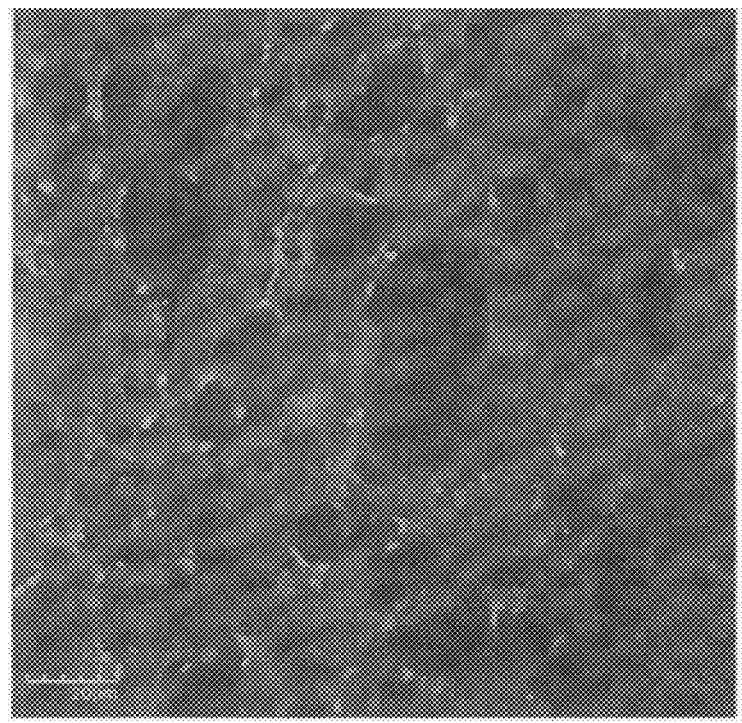
FIG. 4 is an image illustrating a texture of a boiled spaghetti, which is obtained according to a method of Comparative Example 3.

The obtained image is shown in FIG. 4.

As shown in FIG. 4, borders between starches and proteins constituting the internal texture of the spaghetti are unclear, and network structure of glutens and correlation between glutens and starch particles cannot be easily discriminated.

Example 2

Formation of Image of Bread Dough

Preparation of Slice 1 kg of hard wheat flour (Kameria, Nisshin Flour Milling Inc.) was added with 650 ml of water, and the mixture was kneadered to prepare a bread dough by a typical method. The prepared bread dough was rapidly frozen in a quick-freezer (Hoshizaki Electric Co., Ltd.) which is set to −50° C. In addition, a nonfreezing water content was measured by use of a nuclear magnetic resonance apparatus (JNM MU25, JEOL Ltd.). The frozen bread dough was left at −25° C. in a room of a microtome (CM-1100, Leica Corp.) for a duration to give the bread dough having the nonfreezing water content of 17%. Thereafter, the bread dough was sliced to a thickness of 20 μm on a cooling stage, and freeze-fixed on a prepared slide for a microscope, whereby a frozen slice was prepared.

Method for Measuring Nonfreezing Water Content $^1$H (proton) relaxation time, T2, and $^1$H (proton) abundance ratio were measured through a solid echo method (90°-T-90°-T pulse) by use of JNM-MU25 (JEOL Ltd.). The measurement was performed under the following condition: measurement temperature range of −70° C. to 0° C.; pulse width of 2.4 μs; delay time of 8.0 μs; repetition time of 4.0 s; and number of times of integration of 8 times.

Fluorescence Staining

The fluorescent dye prepared in Reference Example 1 was placed in a 200 ml glass bottle, and the frozen slice was immersed in the fluorescent dye. After 30 minutes of immersion, the stained slice was taken out of the glass bottle. Then, extra dye over the surface was wiped away, and the specimen was dried in a draft.

Image Formation

The irradiated specimen was observed by use of a fluorescence microscope. In more specific, an incident-light fluorescence microscope provided with a mirror unit (cube) with a set of fluorescence filters including an excitation filter, a dichroic filter, and an absorption filter was used, and a mercury lamp (major wavelengths: 366 nm, 405 nm, 436 nm, 546 nm and 578 nm) was used as an excitation light source.

Fluorescence emitted from the irradiated specimen was observed under the fluorescence microscope by use of monitoring lights having fluorescence wavelengths of 420 nm, 480 nm, 520 nm, and 580 nm, respectively. Here, the observation was performed through use of an incident-light fluorescence microscope (BX-51, Olympus Optical Co., Ltd.) and at a magnification of 100×.

Figure 5:
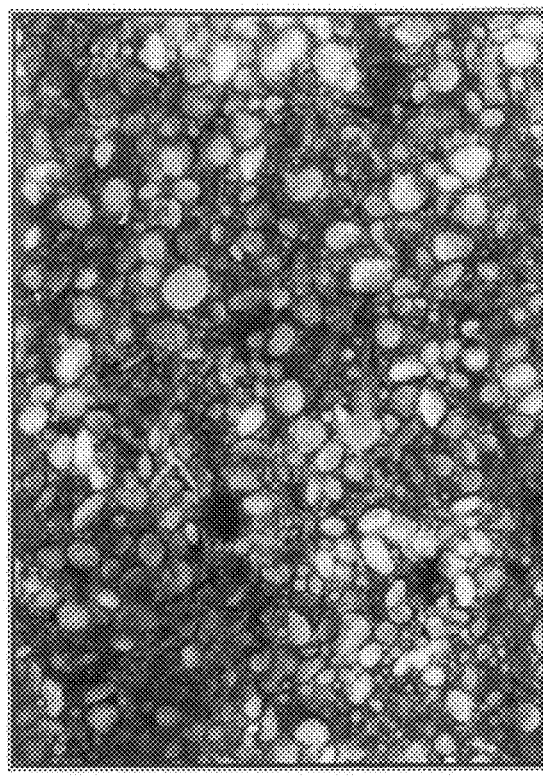
FIG. 5 is an image illustrating a texture of a bread dough, which is obtained according to a method of Example 2 of the present invention.

The obtained image is shown in FIG. 5.

As shown in FIG. 5, borders between starches and proteins constituting the internal texture of the bread dough are clear, and network structure of glutens and correlation between glutens and starch particles can be discriminated easily and clearly, making it possible to discern the structure of the internal texture. This shows us that the present invention can provide a clear image of the internal texture of the bread dough.

Comparative Example 4

Formation of Image of Bread Dough

To provide an example of observation using a fluorescent dye other than the fluorescent dye expressed by Formula 1, staining was performed using Nile Blue of the fluorescent dye prepared in Reference Example 3. The bread dough prepared in Example 2 was rapidly frozen in a manner similar to that described in Example 2. The frozen bread dough was left at −25° C. in a room of a microtome for a duration to give the bread dough having the nonfreezing water content of 18%. For reference, the measurement of the nonfreezing water content was performed in a manner similar to that described in Example 2.

Figure 6:
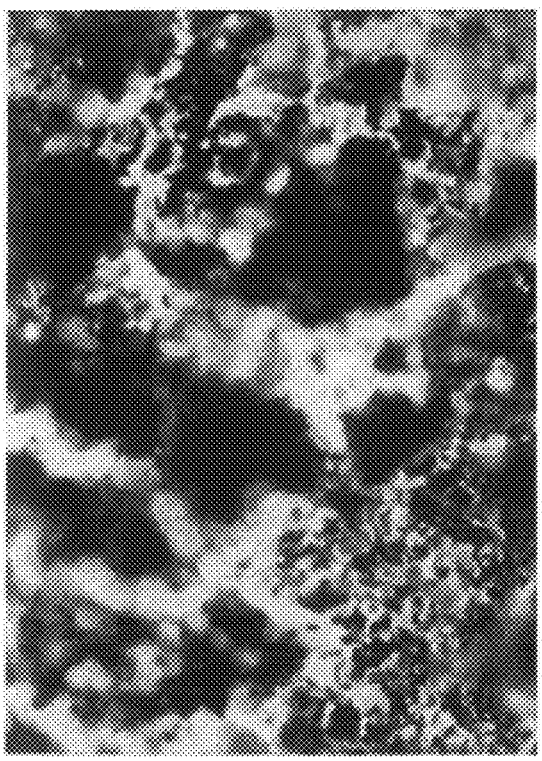
FIG. 6 is an image illustrating a texture of a bread dough, which is obtained according to a method of Comparative Example 4.

The obtained image is shown in FIG. 6.

As shown in FIG. 6, borders between starches and proteins constituting the internal texture of the bread dough are unclear, and network structure of glutens and correlation between glutens and starch particles cannot be easily discriminated.

Example 3

Image Formation of Machine-Made Udon 100 parts by mass of a wheat flour for noodle (White Camellia, Nisshin Flour Milling Inc.) was added with 4 parts by mass of a common salt and 37 parts by mass of water. The mixture was mixed and kneaded in a mixer for 3 minutes at about 80 rpm/min, and for 7 minutes at about 50 rpm/min, and left for 30 minutes to age, whereby a dough for udon was prepared. The obtained dough was rolled to a final noodle thickness of 3.0 mm by use of a typical method, and then cut to noodle strands by use of a cutting blade (#9 cants), whereby a fresh udon was obtained. The obtained fresh udon was boiled in a boiling bath for 15 minutes, immersed in cold water for 30 seconds, and removed water sufficiently. Total water content in the spaghetti after the boiling was controlled to 75%. The udon was rapidly frozen in a manner similar to that described in Example 2. The frozen udon was left at −20° C. in a room of a microtome for a duration to give the udon having the nonfreezing water content of 18%. For reference, the measurement of the nonfreezing water content in the udon was performed in a manner similar to that described in Example 2. An image of the frozen udon was obtained in a manner similar to that described in Example 2. Here, for the fluorescence observation, monitoring lights having fluorescence wavelengths of 440 nm, 500 nm, and 620 nm were used, respectively.

Figure 7:
FIG. 7 is an image illustrating a texture of a machine-made udon (a kind of Japanese wheat noodle), which is obtained according to a method of Example 3 of the present invention.

The obtained image is shown in FIG. 7.

As shown in FIG. 7, borders between starches and proteins constituting the internal texture of the machine-made udon are clear, and a network structure of glutens and correlation between glutens and starch particles can be discriminated, making it possible to discern the structure of the internal texture. In addition, glutens are thin and short, and dispersed arbitrarily, showing that glutens do not have any fixed orientation. As described above, it can be seen that the present invention can provide a clear image of the internal texture of the machine-made udon.

Example 4

Image Formation of Hand-Made Udon

A hand-made dried noodle (flagship store of Inaniwado) was boiled for a duration to give the udon having the total water content of 75%. The udon was rapidly frozen in a manner similar to that described in Example 2. The frozen udon was left at −20° C. in a room of a microtome for a duration to give the udon having the nonfreezing water content of 18%. For reference, the measurement of the nonfreezing water content in the udon was performed in a manner similar to that described in Example 2. An image of the frozen udon was obtained in a manner similar to that described in Example 2. Here, for the fluorescence observation, monitoring lights having fluorescence wavelengths of 440 nm, 500 nm, and 620 nm were used, respectively.

Figure 8:
FIG. 8 is an image illustrating a texture of a hand-made udon, which is obtained according to a method of Example 4 of the present invention.

The obtained image is shown in FIG. 8.

As shown in FIG. 8, borders between starches and proteins constituting the internal texture of the hand-made udon are clear, and a network structure of glutens and correlation between glutens and starch particles can be discriminated, making it possible to discern the structure of the internal texture. It can be seen that a clear image showing the internal texture of the hand-made udon was obtained according to the present invention. In addition, it can be seen that glutens are very long and have a sheaf-like shape, and they have a certain orientation. As described above, according to the present invention, the hand-made udon can be distinguished from the machine-made udon instantly.

Example 5

Formation of Stereoscopic Image of Glutens in Internal Texture of Hand-Made Udon The following processing was performed on the digital color image of the internal textural structure of the hand-made udon of Example 4 to form a stereoscopic image.

Figure 9:
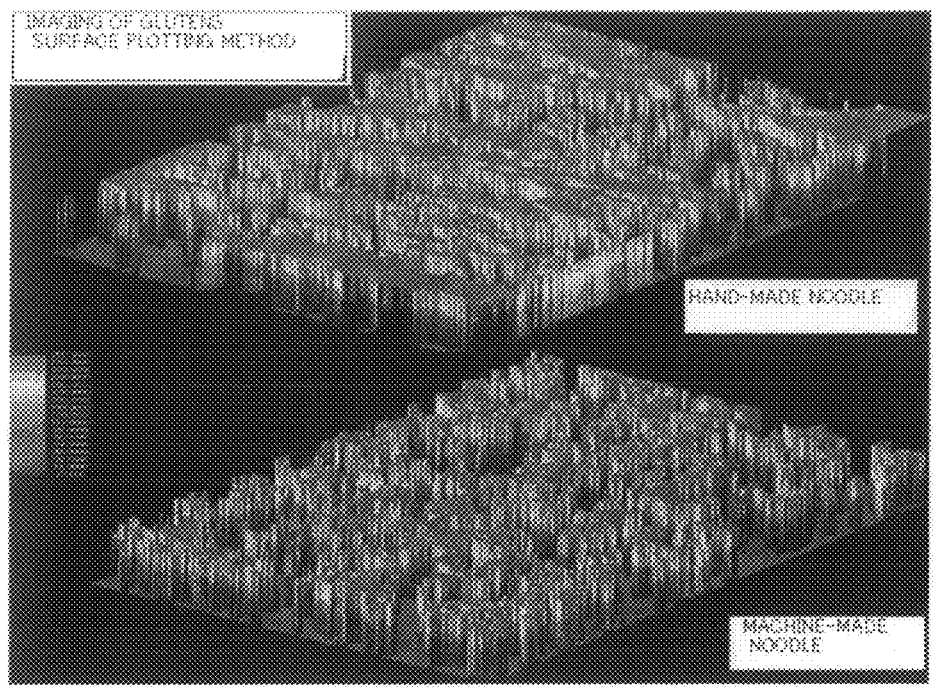
FIG. 9 is a stereoscopic-image-treated textural image illustrating glutens in internal textures of a hand-made udon and a machine-made udon, which is obtained according to a method of Example 5 of the present invention.

Red (R) component of the color image shows the gluten texture in the udon, and thus only the red components were extracted from the RGB data to extract the glutens. The extracted red components were further processed to 256 tone binarized image. That is, the gluten was converted to black (1), and the others were converted to white (0). On the basis of this image, the stereoscopic processing was performed only on the surface data of the glutens through surface rendering, whereby an image was obtained. The obtained image is shown in FIG. 9. Through the above-described image processing, it became possible to protrude only the glutens clearly over the digital image in three dimensions.

Further, the above-described processing was performed on the digital color image of the internal textural structure of the machine-made udon of Example 3 to form a stereoscopic image. The obtained image is shown in FIG. 9. Through the above-described image processing, it became possible to protrude only the glutens clearly over the digital image in three dimensions.

Example 6

Formation of Image of Soft Biscuit Dough

40% by mass of soft wheat flour (Violet, Nisshin Flour Milling Inc.), 30% by mass of sugar, 25% by mass of shortening, 3% by mass of common salt, and 2% by mass of baking powder were mixed together to prepare a soft biscuit dough by use of a typical method. The soft biscuit dough was rapidly frozen in a manner similar to that described in Example 2. The frozen soft biscuit dough was left at −23° C. in a room of a microtome for about 10 minutes. The nonfreezing water content in the soft biscuit dough at this time was 15%. For reference, the measurement of the nonfreezing water content in the soft biscuit dough was performed in a manner similar to that described in Example 2. An image of the frozen soft biscuit dough was obtained in a manner similar to that described in Example 2. Here, for the fluorescence observation, monitoring lights having fluorescence wavelengths of 440 nm, 520 nm, and 580 nm were used, respectively. In addition, the fluorescent dye used herein was the fluorescent dye of Reference Example 2.

Figure 10:
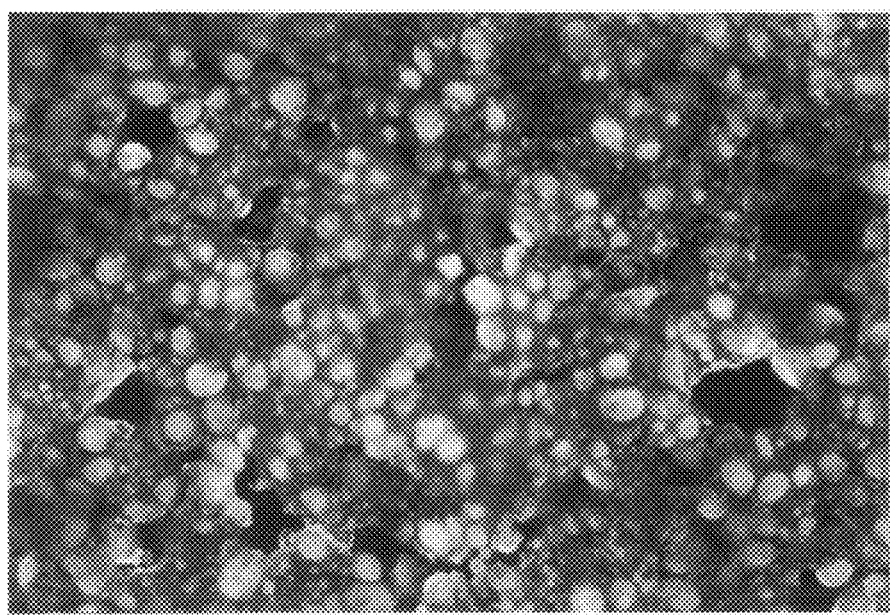
FIG. 10 is an image illustrating a texture of a soft biscuit dough, which is obtained according to a method of Example 6 of the present invention.

The obtained image is shown in FIG. 10.

As shown in FIG. 10, borders between starches, proteins and lipids constituting the internal texture of the soft biscuit dough are clear, and a network structure of glutens and correlation between glutens, starch particles, and lipid particles can be discriminated, making it possible to discern the structure of the internal texture. In addition, it can be seen that the internal texture has a bubble-type structure containing a large number of air. As described above, it can be seen that the present invention can provide a clear image of the internal texture of the soft biscuit dough.

Example 7

Formation of Image of Hard Biscuit Dough

76% by mass of soft wheat flour (Violet, Nisshin Flour Milling Inc.), 15% by mass of sugar, 5% by mass of shortening, 2% by mass of common salt, and 2% by mass of baking powder were mixed together to prepare a hard biscuit dough by use of a typical method. The hard biscuit dough was rapidly frozen in a manner similar to that described in Example 2. The frozen hard biscuit dough was left at −23° C. in a room of a microtome for about 10 minutes. The nonfreezing water content in the hard biscuit dough at this time was 14%. For reference, the measurement of the nonfreezing water content in the hard biscuit dough was performed in a manner similar to that described in Example 2. An image of the frozen hard biscuit dough was obtained in a manner similar to that described in Example 2. Here, for the fluorescence observation, monitoring lights having fluorescence wavelengths of 440 nm, 520 nm, and 580 nm were used, respectively. In addition, the fluorescent dye used herein was the fluorescent dye of Reference Example 2.

Figure 11:
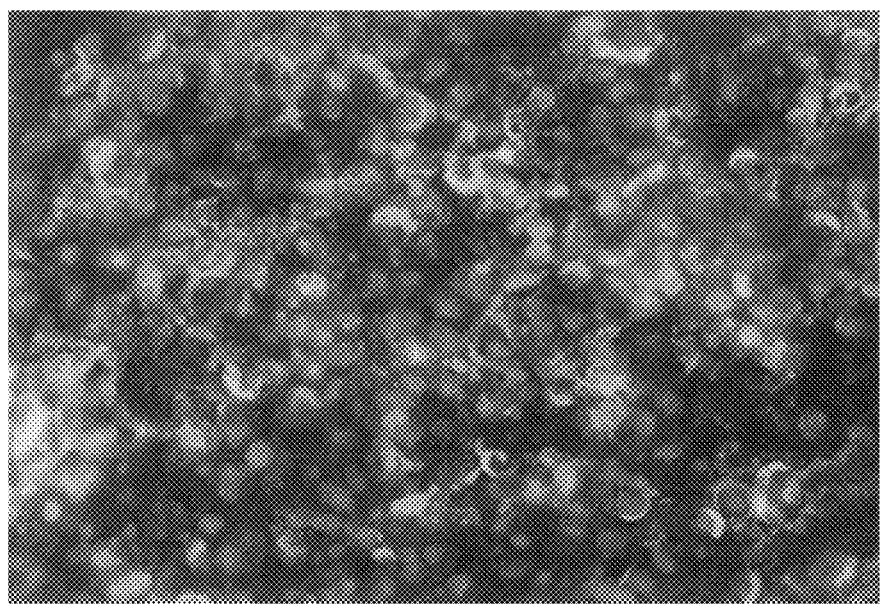
FIG. 11 is an image illustrating a texture of a hard biscuit dough, which is obtained according to a method of Example 7 of the present invention.

The obtained image is shown in FIG. 11.

As shown in FIG. 11, borders between starches, proteins and lipids constituting the internal texture of the hard biscuit dough are clear, and a network structure of glutens and correlation between glutens, starch particles, and lipid particles can be discriminated, making it possible to discern the structure of the internal texture. In addition, it can be seen that the internal texture has little airs, has a dense lamellar structure. As described above, it can be seen that the present invention can provide a clear image of the internal texture of the hard biscuit dough.

What is claimed is:

1. A method for forming a textural structure image of a processed food or a raw material for the processed food, the method comprising:
    freezing the processed food or the raw material for the processed food at −18° C. or less and adjusting a nonfreezing water content of the frozen processed food or the frozen raw material for the processed food to 30% by weight or less,
    preparing a slice of the frozen processed food or the frozen raw material for the processed food having a nonfreezing water content of 30% by weight or less,
    staining the slice of the frozen processed food or the frozen raw material for the processed food having a nonfreezing water content of 30% by weight or less with a fluorescent dye having a triphenylmethane skeleton to provide a specimen;
    radiating an excitation light to the specimen;
    observing the radiated specimen by use of three or more kinds of monitoring lights including at least a monitoring light (A) having a fluorescence wavelength of 380 nm or longer and shorter than 450 nm, a monitoring light (B) having a fluorescence wavelength of 450 nm or longer and shorter than 560 nm, and a monitoring light (C) having a fluorescence wavelength of 560 nm to 700 nm; and
    forming an image on the basis of a result of the observation.

2. The method according to claim 1, wherein the nonfreezing water content of the frozen processed food or the frozen raw material for the processed food is adjusted to 14 to 30% by weight.

3. The method according to claim 1 or 2, wherein, the processed food is a secondary processed food of a grain, and the raw material for the processed food is a grain or a primary processed food of a grain to be subsequently subjected to a secondary processing.

4. The method according to claim 1, wherein the fluorescent dye having a triphenylmethane skeleton is expressed by the following formula:

[Formula 1]

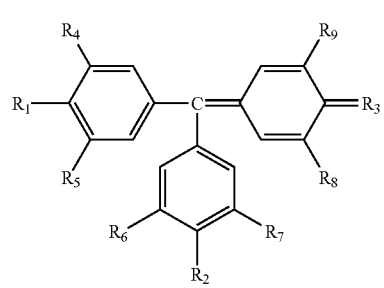

wherein, $R_1$ and $R_2$ each represent $NH_2$, NHY, $NY^1Y^2$, or OH; $R_3$ represents O, $NH_2$, NHY, or $NY^1Y^2$; $R_4$, $R_5$, $R_6$, $R_7$, $R_8$, and $R_9$ each represent one selected from H, $C_nH_{2n+1}$, $SO_3X$, and COOX, where X represents H or an alkali metal atom, Y, $Y^1$, and $Y^2$ each represent an alkyl group having a carbon number of 1 to 3, or a phenyl group which may have a substituent, and n represents an integer of 1 to 3.

* * * * *